United States Patent [19]

Oertle et al.

[11] Patent Number: 4,695,643

[45] Date of Patent: Sep. 22, 1987

[54] SILANES, PROCESS FOR THEIR PREPARATION, AND THEIR USE

[75] Inventors: Konrad Oertle; Hansjürg Wetter, both of Therwil, Switzerland

[73] Assignee: Ciba-Geigy Corporation, Ardsley, N.Y.

[21] Appl. No.: 782,349

[22] Filed: Oct. 1, 1985

[30] Foreign Application Priority Data

Oct. 4, 1984 [CH] Switzerland ............... 4765/84-0

[51] Int. Cl.⁴ ................... C07F 7/08; C07F 7/10; C07F 7/18

[52] U.S. Cl. .................... 556/428; 556/427; 556/406; 556/442; 556/465; 556/479; 556/482; 556/489

[58] Field of Search ........... 556/465, 428, 427, 442, 556/482, 479, 489, 406

[56] References Cited

U.S. PATENT DOCUMENTS

| | | | |
|---|---|---|---|
| 2,626,268 | 1/1953 | Barry et al. | 556/465 X |
| 2,642,447 | 6/1953 | Plueddemann | 556/465 X |
| 2,684,974 | 7/1953 | Hatcher et al. | 556/465 X |
| 4,254,271 | 3/1981 | Finke et al. | 556/479 |
| 4,297,499 | 10/1981 | Koga et al. | 556/465 |

OTHER PUBLICATIONS

J. of Organom. Chem 225, pp. 177–191 (1982).
Synthetic Communications 9(4), 295–299 (1979).
"Chemie und Technologie der Silicone", Verlag Chemie, Weinheim, pp. 44–49 (1968).

*Primary Examiner*—Paul F. Shaver

*Attorney, Agent, or Firm*—Luther A. R. Hall

[57] ABSTRACT

Compounds of the formula Ia

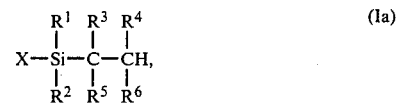

in which X and $R^1$ to $R^6$ are as defined in the claims, are obtainable by reacting monochlorosilanes of the formula II

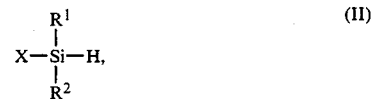

with tetrasubstituted ethylenes of the formula III

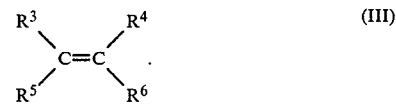

X as Cl and Br can be replaced by ester groups of inorganic and organic acids. The compounds of the formula I and those with other ester groups are suitable especially as a protective-group reagent for hydroxyl, mercapto, carboxyl, amino and amide groups.

9 Claims, No Drawings

SILANES, PROCESS FOR THEIR PREPARATION, AND THEIR USE

The present invention relates to silanes having a 1,1,2,2-tetrasubstituted ethyl radical, a process for its preparation by addition of monochloromonohydrosilanes to tetrasubstituted ethylenes and to the use of the silanes as a protective-group reagent.

It is known from D. Seyferth et al., J. of Organom. Chem., 225, pages 177-191 (1982), that (1,1,2,2-tetramethyl-ethyl)-dimethylchlorosilane is obtainable by ring opening of hexamethylsilirane with hydrogen chloride. It is also known that monochlorosilanes can be prepared by the addition of $R^aR^bSiHCl$ to unsaturated compounds (cf. W. Noll, Chemie und Technologie der Silicone [Chemistry and Technology of the Silicones], Verlag Chemie, Weinheim, (1968), pages 45 et seq.). This reaction is catalysed by metal compounds, for example $H_2PtCl_6$, it frequently being necessary to apply high pressure and/or high temperatures. Rearrangement reactions occur under these conditions, in particular if highly branched alkenes are used.

According to DE-A No. 2,804,204, it is therefore proposed to use aluminium halides of chlorine and bromine as the catalysts for this reaction. In this process, for example 2-methylbut-2-ene, a trisubstituted ethylene, is also used, (1,2-dimethylprop-1-yl)dimethylchlorosilane being obtained in high yields. The addition of, for example, dimethylchlorosilane takes place virtually only on the monosubstituted carbon atom of the trisubstituted ethylene, and not on the disubstituted carbon atom. Neither is it described in other specialist literature that the addition could take place on the disubstituted carbon atom of an ethylene.

The present invention relates to compounds of the formula I

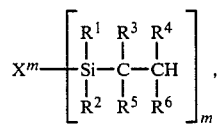

in which X is an ester group of an inorganic or organic acid and m is a number from 1 to 4, $R^1$ and $R^2$ independently of one another are linear or branched $C_1$-$C_{12}$-alkyl or unsubstituted or $C_1$-$C_6$-alkyl-substituted benzyl, $C_5$-cycloalkyl or $C_6$-cycloalkyl, or $R^1$ and $R^2$ together are tetramethylene or pentamethylene and $R^3$ to $R^6$ independently of one another are linear or branched $C_1$-$C_{12}$-alkyl, unsubstituted or $C_1$-$C_6$-alkyl-substituted phenyl or phenyl$C_nH_{2n}$- with n =1 to 6, $C_5$-cycloalkyl or $C_6$-cycloalkyl, $R^3$ and $R^5$ together and/or $R^4$ and $R^6$ together are tetramethylene or pentamethylene, or $R^3$ and $R^4$ together and/or $R^5$ and $R^6$ together are trimethylene or tetramethylene, one of the radicals $R^1$ to $R^6$ containing at least two carbon atoms if X is Cl.

An ester group X preferably is a radical of a monobasic to tetrabasic inorganic or organic acid, from which at least one acidic H atom has been removed.

The inorganic acids can be oxygen acids and oxygen-free acids. Amongst the latter, hydrochloric and hydrobromic acids (X = Cl or Br) are preferred. Examples of suitable oxygen acids are $H_2SO_4$, $FSO_3H$, $HClO_4$, $H_3PO_3$ and $H_3PO_4$. Other suitable oxygen acids are sulfonic acids, for example alkylsulfonic and arylsulfonic acids such as methylsulfonic acid, phenylsulfonic acid or paramethylphenylsulfonic acid or, for example, partially fluorinated or perfluorinated sulfonic acids such as fluoromethylsulfonic acid, difluoromethylsulfonic acid and trifluoromethylsulfonic acid.

Examples of suitable organic acids are aliphatic and aromatic carboxylic acids, such as formic acid, acetic acid, chloroacetic acid, trichloroacetic acid, fluoroacetic acid, trifluoroacetic acid, propionic acid, oxalic acid, malonic acid, succinic acid, adipic acid, cyclohexanecarboxylic acid, cyclohexane-1,4-dicarboxylic acid, benzoic acid, phenylacetic acid, terephthalic acid, isophthalic acid, trimellitic acid and pyromellitic acid.

Particularly preferably X is —Cl, —Br, $CH_3SO_3$— or $CF_3SO_3$—and especially Cl.

In formula I, m preferably is one of the numbers 1 to 3, in particular 1 or 2 and especially the number 1.

In a preferred embodiment, $R^1$ and $R^2$ are identical radicals. Preferably, $R^1$ and $R^2$ are $C_1$-$C_6$-alkyl, especially $C_1$-$C_4$-alkyl.

Examples of alkyls $R^1$ and $R^2$ as well as $R^3$ to $R^6$ are methyl, ethyl, n-propyl, isopropyl, n-butyl, isobutyl, tertiary-butyl, pentyl, hexyl, heptyl, octyl, decyl and dodecyl. Particularly preferably, $R^1$ and $R^2$ are methyl.

Examples of substituted benzyls $R^1$ and $R^2$ are trimethylbenzyl, propylbenzyl, butylbenzyl, methylbenzyl, ethylbenzyl and dimethylbenzyl.

Examples of cycloalkyls $R^1$ and $R^2$ are cyclopentyl, methylcyclopentyl, cyclohexyl and methylcyclohexyl.

Alkyls $R^3$ to $R^6$ preferably contain 1 to 6 carbon atoms, especially 1 to 4 carbon atoms. Examples of $R^1$ and $R^2$ have been mentioned. The preferred alkyl radicals are methyl, ethyl, propyl and butyl.

Substituted phenyls $R^3$ to $R^6$ can, for example, be methylphenyl, dimethylphenyl or ethylphenyl. In the formula phenyl—$C_nH_2$—, n is preferably 1 or 2. Examples are benzyl, methylbenzyl, ethylbenzyl, phenylethyl and methylphenylethyl.

In a preferred embodiment, $R^3$ to $R^6$ in the formula I are independently of one another $C_1$-$C_6$-alkyl, cyclopentyl or cyclohexyl, or $R^3$ and $R^5$ and/or $R^4$ and $R^6$ are pentamethylene or $R^3$ and $R^4$ and/or $R^5$ and $R^6$ are tetramethylene.

In another preferred embodiment, alkyls $R^3$ to $R^6$ independently of one another are methyl, ethyl, propyl, ipropyl, n-butyl, i-butyl or t-butyl.

In a further preferred embodiment, X is Cl and $R^1$ and $R^2$ are methyl, and one of the radicals $R^3$ to $R^6$ is ethyl and the others are methyl, or $R^3$ and $R^4$ are ethyl and $R^5$ and $R^6$ are methyl, or $R^3$ to $R^6$ are ethyl.

It has been found, surprisingly, that compounds of the formula Ia, in which X is Cl or Br, are obtained in high yields and purities when the addition of disubstituted chlorosilanes to tetrasubstituted ethylenes is catalysed by aluminium halides. In spite of the high degree of branching, virtually no isomerisations of the tetrasubstituted ethylenes are observed.

The invention also relates to the process for the preparation of compounds of the formula Ia

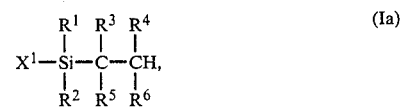

in which $X^1$ is Cl or Br, $R^1$ and $R^2$ independently of one another are linear or branched $C_1$-$C_{12}$-alkyl, $C_5$-cycloalkyl or $C_6$-cycloalkyl or unsubstituted or $C_1$-C-

6-alkylsubstituted benzyl, or $R^1$ and $R^2$ together are tetramethylene or pentamethylene, and $R^3$ to $R^6$ independently of one another are linear or branched $C_1$-$C_{12}$-alkyl, unsubstituted or $C_1$-$C_6$-alkyl-substituted phenyl or phenyl-$C_nH_{2n}$-with n=1 to 6, $C_5$-cycloalkyl or $C_6$-cycloalkyl, $R^3$ and $R^5$ together and/or $R^4$ and $R^6$ together are tetramethylene or pentamethylene, or $R^3$ and $R^4$ together and/or $R^5$ and $R^6$ together are trimethylene or tetramethylene, by addition of a monohalogenosilane of the formula II

in which $R_1$, $R_2$ and X are as defined above, to substituted ethylene in the presence of catalytic amounts of aluminium trichloride, aluminium tribromide, alkylaluminium dichloride, alkylaluminium dibromide, aluminium oxide-chloride, aluminium oxide-bromide or mixtures thereof at temperatures of at most 60° C., wherein the ethylene is a tetrasubstituted ethylene of the formula III

in which $R^3$ to $R^6$ are as defined above.

The preferred meanings given above apply to $R^1$ to $R^6$, and additionally $R^1$ to $R^6$ can also be methyl.

The alkyl group in an alkylaluminium dichloride or dibromide preferably contains 1 to 12, in particular 1 to 6 and especially 1 to 4 carbon atoms. Examples are methyl, ethyl, n-propyl, i-propyl, n-butyl, i-butyl, t-butyl, pentyl, hexyl, octyl, decyl and dodecyl.

The catalyst used is preferably $AlCl_3$ and/or $C_1$-$C_4$-alkyl-$AlCl_2$. The reaction temperature preferably is 0° to 60° C., in particular 20° to 40° C. The reaction is exothermic and cooling is necessary in general in order to maintain the reaction temperature. The catalyst can be used in amounts of 0.01 to 20% by weight, in particular 0.1 to 10 % by weight and especially 0.1 to 5% by weight, relative to the reactants.

The reaction is preferably carried out under a blanketing gas atmosphere, for example nitrogen, helium or argon. Application of a positive pressure is advantageous when gaseous reactants are employed. Since the reactants are liquids in most cases, the use of inert solvents is superfluous. To avoid the formation of hydrolysed by-products, exclusion of moisture must be ensured.

The reaction products are worked up by conventional methods, the catalyst being generally separated off first, for example by addition of the solvent (hydrocarbons) for the reaction product and filtration. The solvent can then be removed and the crude product can be purified by known processes, for example by distillation and/or chromatographic methods. In many cases, the desired silane can be isolated by direct distillation of the reaction mixture.

Compounds of the formula I, in which X is the ester group of an oxygen acid, can be prepared by reacting compounds of the formula Ia with oxygen acids, with elimination of HBr or HCl, in a manner known per se. The reaction can be carried out in an inert solvent and, if appropriate, with the addition of bases such as tertiary amines, in order to fix the HCl or HBr formed.

Examples of suitable inert solvents are substituted or unsubstituted hydrocarbons, ethers and esters.

The compounds of the formula I including (1,1,2,2-tetramethyl-eth-1-yl)-dimethylchlorosilane are outstandingly suitable as a protective-group reagent. Compared with known silylation reagents, for example tertiary-butyldimethylchlorosilane [cf. Synthetic Communications, 9(4), 295-299 (1979)] or (1,1,2-trimethyleth-2-yl)-dimethylchlorosilane (cf. DE-A No. 2,804,204), they have a substantially improved hydrolytic stability. In addition, the compounds have a more pronounced lypophilic character which can be influenced by the number of carbon atoms in the $R^3$ to $R^6$ groups and thus adapted to specific reaction conditions. Due to the improved hydrolytic stability, the reaction medium can be varied more widely.

The invention also relates to the use of compounds of the formula Ib

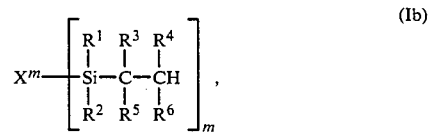

in which X is an ester group of an inorganic or organic acid and m is an integer from 1 to 4, $R^1$ and $R^2$ independently of one another are linear or branched $C_1$-$C_{12}$-alkyl, $C_5$-cycloalkyl or $C_6$-cycloalkyl or unsubstituted or $C_1$-$C_6$-alkylsubstituted benzyl, or $R^1$ and $R^2$ together are tetramethylene or pentamethylene and $R^3$ to $R^6$ independently of one another are linear or branched $C_1$-$C_{12}$-alkyl, unsubstituted or $C_1$-$C_6$-alkyl-substituted phenyl or phenyl-$C_nH_{2n}$-with n=1 to 6, $C_5$-cycloalkyl or $C_6$-cycloalkyl, $R^3$ and $R^5$ together and/or $R^4$ and $R^6$ together are tetramethylene or pentamethylene or $R^3$ and $R^4$ together and/or $R^5$ and $R^6$ together are trimethylene or tetramethylene, as a removable protective-group reagent for hydroxyl, mercapto, carboxyl, amino and amide groups.

The present invention also relates to a process for protecting hydroxyl, mercapto, carboxyl, amino and amide groups in organic syntheses, which comprises reacting an organic compound carrying hydroxyl, mercapto, carboxyl groups or alkali metal salts thereof, amino and/or amide groups, or an aldehyde or ketone having an δ-H atom, with a compound of the formula I

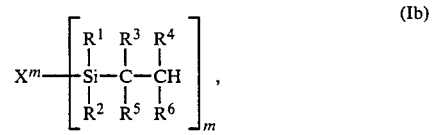

and, after the synthesis reaction has been carried out, eliminating the protective group in a manner known per se.

The preferred meanings given above apply to $R^1$ to $R^6$, and $R^1$ to $R^6$ preferably can also be methyl. Examples of suitable alkali metal salts of alcohols, thiols and carboxylic acids are the lithium salts and in particular the sodium salts.

The amino or amide groups can be partially substituted by aliphatic or aromatic groups. The amide group can also be present in the form of a lactam.

Suitable aldehydes and ketones are of the formulae IV and V

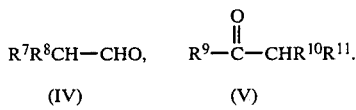

In the reaction with a protective-group reagent of the formula Ib, vinyl silyl ethers of the formulae IVa and Va

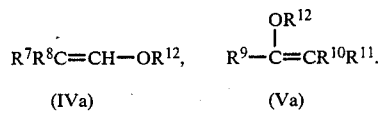

are then formed.

$R^7$, $R^8$, $R^{10}$ and $R^{11}$ are hydrogen atoms or organic radicals which contain preferably 1 to 30, in particular 1 to 20 and especially 1 to 16 carbon atoms. $R^9$ is such an organic radical. $R^{12}$ is the radical

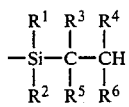

Examples of organic radicals $R^7$, $R^8$, $R^9$, $R^{10}$ and $R^{11}$ are aliphatic, cycloaliphatic, heterocyclic, aromatic or heteroaromatic radicals. The radicals can be unsubstituted or substituted by, for example, $C_1$-$C_{12}$-alkyl, $C_1$-$C_{12}$-alkoxy, $C_1$-$C_{12}$-alkylthio, halogen, such as F, Cl and Br, phenyl or benzyl.

The aliphatic radical can be linear or branched alkyl, in particular alkyl having 1 to 12 carbon atoms. The cycloaliphatic radical can contain 3 to 12, in particular 3 to 7 ring carbon atoms. The heterocyclic radical can contain 1 to 3 hetero-atoms and 3 to 7 ring members in total. The heteroaromatic radical preferably contains 1 or 2 hetero-atoms and preferably 5 or 6 ring members in total. The aromatic radical is preferably phenyl, naphthyl, anthranyl or phenanthryl.

$R^7$ and $R^8$ as well as $R^9$ and $R^{10}$ can, together with the carbon atoms to which they are linked, also form a cycloaliphatic or heterocyclic radical having 3 to 7 ring members in total and preferably 1 or 2 hetero-atoms. The heterocyclic radicals are not bonded via heteroatoms to the CH groups or CO groups in the formulae IV and V.

The protective group is introduced in the conventional manner under mild conditions, in most cases at room temperature up to temperatures of about 100° C., by reacting a compound of the formula I with a compound which contains the group to be protected (latent), if appropriate in the presence of an organic base as an acceptor for acids formed. Preferred suitable organic bases are tertiary amines, for example trimethylamine, triethylamine, tributylamine, N-methylpiperidine, N-methylpyrrolidine, pyridine or imidazole. The reaction is in general carried out in the presence of inert solvents. Polar solvents such as ethers, N-substituted lactams or N-disubstituted acid amides, for example dioxane, dibutyl ether, tetrahydrofuran, dimethylformamide, dimethylacetamide, hexamethylphosphoric acid triamide and N-methylpyrrolidone are particularly suitable.

The protected compound is isolated by conventional methods, for example by distillation, crystallisation or chromatography.

The preparation of compounds with a protective group according to the invention from compounds of low reactivity, for example tertiary alcohols, is advantageously carried out in such a way that corresponding silyl esters of strong acids, for example trifluoromethanesulfonic acid, are reacted in the presence of a base with a compound containing the group which is to be protected.

The silyl-protective group is eliminated in accordance with conventional methods by the action of aqueous acids or bases, optionally in the presence of inert solvents, by the action of Lewis acids, of quaternary ammonium fluorides or the action of HF/urea mixtures. The silanol formed in the hydrolysis can be converted in a simple manner, for example with $SOCl_2$ or $PCl_3$ or $PCl_5$, into the chlorosilane of the formula Ia.

The examples which follow explain the invention in more detail. (A) Preparation of monochlorosilanes

EXAMPLE 1

Preparation of (1,1,2,2-tetramethyleth-1-yl)dimethylchlorosilane.

100 ml (0.92 mol) of dimethylchlorosilane and 3.8 g (0.028 mol) of aluminium chloride are introduced into a 500 ml three-necked flask with a reflux condenser and dropping funnel. Within 1 hour, 109.5 ml (0.92 mol) of tetramethylethylene are added dropwise. The reaction temperature is maintained in the range from 25° to 30° C. by external cooling. After 4 hours, undissolved aluminium chloride is filtered off from the reaction solution which is then distilled.

This gives 141 g of product (86% yield), boiling point: 62°-64° C./20.8 mbar. The $^1$H-NMR spectrum is in agreement with the structure.

EXAMPLE 2

Preparation of (1,1,2,2-tetraethyl-eth-1-yl) dimethylchlorosilane.

2.1 g of tetraethylethylene, 2 ml (18 mmol) of dimethylchlorosilane and 200 mg of $AlCl_3$ are reacted according to Example 1. After 2 hours, the reaction mixture is diluted with pentane and the precipitate is filtered off. The pentane is stripped from the filtrate in vacuo and the residue is distilled. This gives 2.8 g (80 % of theory) of product as a colourless liquid. Boiling point = 75°-80° C./0.195 mbar.

Analysis: calculated: C 61.36 H 11.59 Cl 15.09 Si 11.96 ($C_{12}H_{27}ClSi$); found: C 61.69 H 11.49 Cl 14.88 Si 12.08.

EXAMPLE 3

Preparation of (1,2-diethyl-1,2-dimethyleth-1-yl) dimethylchlorosilane.

According to Example 2, 200 mg of 3,4-dimethylhex-3-ene, 0.2 ml (1.8 mmol) of dimethylchlorosilane and 50 mg (0.37 mmol) of $AlCl_3$ are reacted and the product is worked up. This gives 180 mg (50% of theory) of colourless liquid of boiling point = 95°-97° C./0.26 mbar.

EXAMPLE 4

Preparation of

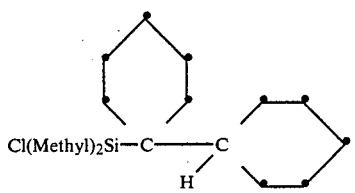

According to Example 2, 1.1 g of

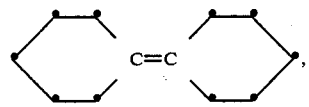

1 ml (9 mmol) of dimethylchlorosilane and 150 mg of AlCl$_3$ are reacted and the product is worked up. This gives 1.2 g (67% of theory) of a colourless oil of boiling point = 100°–105° C./0.065 mbar.

EXAMPLE 5

Preparation of

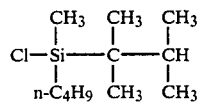

12.0 g (0.088 mol) of methyl-butyl-chlorosilane, prepared from methyl-dichlorosilane and n-butyl-lithium, and 1.17 g (8.8 mmol) of aluminium chloride are introduced into a 100 ml three-necked flask with reflux condenser and dropping funnel. Within 15 minutes, 7.4 g (0.088 mol) of tetramethylethylene are added dropwise. The reaction temperature is maintained in the range from 20° to 25° C. by external cooling. After one hour, the product is isolated by distillation.

This gives 15.6 g of product, boiling point: 98°–100° C./20.8 mbar (80% of theory). The $^1$H-NMR spectrum is in agreement with the structure.

EXAMPLE 6

Ethyl-aluminium dichloride as the catalyst 1.03 ml (10 mmol) of ethyl-aluminium dichloride are introduced in 21.6 ml (0.2 mol) of dimethylchlorosilane into a 100 ml three-necked flask with reflux condenser and dropping funnel. Witnin 30 minutes, 23.9 ml (0.2 mol) of tetramethylethylene are added dropwise. The reaction temperature is maintained in the range from 20° to 25° C. by external cooling. After one hour, the reaction solution is distilled.

This gives 22.1 g of product (62% of theory), boiling point: 62°–64° C./20.8 mbar.

EXAMPLE 7

Isopropyl-aluminium dichloride as the catalyst 1.37 ml (10 mmol) of isopropyl-aluminium dichloride are introduced into 21.6 ml (0.2 mol) of dimethylchlorosilane into a 100 ml three-necked flask with reflux condenser and dropping funnel. Within 30 minutes 23.9 ml (0.2 mol) of tetramethylethylene are added dropwise. The reaction temperature is maintained in the range from 20° to 25° C. by external cooling. After one hour, the reaction solution is distilled.

This gives 25.9 g of product (72% of theory), boiling point: 62–64° C./20.8 mbar.

(B) Application examples

EXAMPLE 8

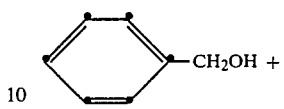

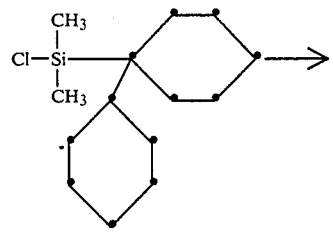

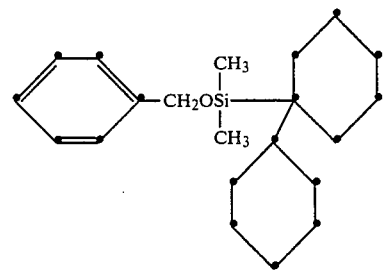

1 g (3.86 mmol) of the silyl chloride are added to a mixture of 0.31 g (4.5 mmol) of imidazole and 0.46 g (4.3 mmol) of benzyl alcohol in 5 ml of DMF. After stirring at room temperature for 16 hours, working-up is carried out as follows: the reaction mixture is diluted with hexane and washed several times with water. The organic phase is then dried with MgSO$_4$ and evaporated. After chromatography on silica gel, 1.77 g of the desired silyl ether (92% of theory) are isolated as a colourless oil.

Analysis: calculated: C 76.30; H 10.37; Si 8.50; (C$_{21}$H$_{34}$OSi) found: C 76.32; H 10.36; Si 8.71.

EXAMPLE 9

Preparation of:

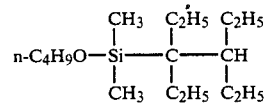

2.0 g (8.5 mmol) of (1,1,2,2-tetraethyleth-1-yl)dimethylchlorosilane are, as described in Example 8, stirred with 519 mg (7 mmol) of n-butanol in the presence of 578 mg (8.5 mmol) of imidazole in 5 ml of DMF for 16 hours at room temperature. The mixture is worked up as described in Example 8.

After chromatography on silica gel and subsequent distillation, 1.71 g (90% of theory) of a colourless oil of boiling point = 80°–85° C./0.0665 mbar are isolated.

Analysis:

(C$_{16}$H$_{36}$OSi) calculated: C 70.51; H 13.31; Si 10.31; found: C 70.25; H 13.19; Si 10.3.

EXAMPLE 10

Preparation of

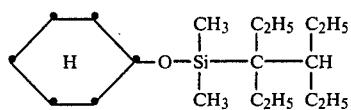

The reaction is carried out in accordance with Example 9, with cyclohexanol in place of n-butanol. This gives a colourless oil of boiling point =100°-105° C./0.039 mbar.

Analysis:
($C_{18}H_{38}OSi$) calculated: C 72.41; H 12.83; Si 9.41; found: C 72.20; H 12.99; Si 9.81.

EXAMPLE 11

Preparation of

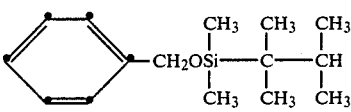

Analogously to Example 8, 1.08 g (10 mmol) of benzyl alcohol are reacted in the presence of 1.02 g (15 mmol) of imidazole in 10 ml of DMF with 1.95 g (11 mmol) of (1,1,2,2,-tetramethyleth-1-yl)-dimethylchlorosilane for 16 hours at room temperature. After distillation of the crude product, 2.15 g (86% of theory) of a colourless oil of boiling point 105°-110° C./0 026 mbar are obtained.

Analysis:
($C_{15}H_{26}OSi$) calculated: C 71.93; H 10.46; Si 11.21; found: C 71.80; H 10.38; Si 11.34.

EXAMPLE 12

Preparation of

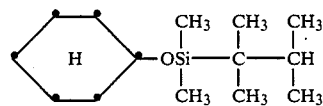

Analogously to Example 8, 1.0 g (10 mmol) of cyclohexanol are reacted in the presence of 1.02 g (15 mmol) of imidazole in 10 ml of DMF with 1.96 g (11 mmol) of (1,1,2,2-tetramethyleth-1-yl)-dimethylchlorosilane for 16 hours at room temperature. The mixture is worked up as described and, after distillation of the crude product, 2.25 g (93% of theory) of colourless oil of boiling point =49°-51° C./0.026 mbar are obtained.

Analysis:
($C_{14}H_{30}SiO$) calculated: C 69.35; H 12.47; Si 11.58; found: C 69.37; H 12.23; Si 12.01.

EXAMPLE 13

Preparation of

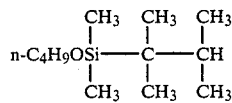

The reaction is carried out in accordance with Example 8, using
5.19 g (70 mmol) of n-butanol,
7.15 g (0.105 mmol) of imidazole
13.74 g of (1,1,2,2-tetramethyleth-1-yl)-dimethylchloro silane in
50 ml of dimethylformamide (DMF).

Yield: 13.17 g (87 % of tneory); boiling point =104°-106° C./26 mbar.

Analysis:
($C_{12}H_{38}SiO$) calculated: C 66.59; H 13.04; Si 12.98; found: C 66.41; H 13.13; Si 13.34.

EXAMPLE 14

Preparation of:

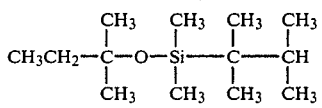

(a) Preparation of (1,1,2,2-tetramethyleth-1-yl)-dimethylsilyl trifluoromethanesulfonate 50 ml of trifluor-methanesulfonic acid are slowly added dropwise at room temperature under argon to 101.57 g (0.57 mol) of (1,1,2,2-tetramethyleth-1-yl)-dimethylchlorosilane. Subsequently, the mixture is heated for 8 hours at 60° C. After this time, the evolution of HCl ceases. 111 g (67% of theory) of a colourless oil of boiling point =123°-124° C./28.6 mbar are obtained by distillation. The $^1$H-NMR spectrum is in agreement with the structure. (b) Reaction of the silyl ester according to (a) with 2-methylbutan-2ol.

A mixture of 9.75 g (0.091 mol) of 2,6-lutidine and 6.17 g (0.07 mol) of 2-methyl-2-butanol is added dropwise at 0° C. under argon to 22.44 g (0.07 mol) of the silyl ester in 100 ml of methylene chloride. After stirring at room temperature for 4 hours, the mixture is poured on ice and extracted with hexane.

The combined hexane phases are washed with water, dried with $MgSO_4$ and concentrated in vacuo. From 15.65 g of crude product, 13.5 g of a colourless oil (84% of theory) of boiling point 118°-120° C./30 mbar are isolated by distillation.

Analysis:
($C_{13}H_{30}SiO$) calculated: C 67.75; H 13.12; Si 12.19; found: C 68.01; H 12.96; Si 12.52.

EXAMPLE 15

Preparation of

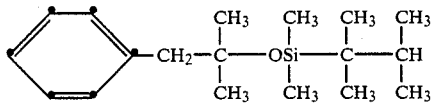

20.44 g (0.07 mol) of the silyl ester according to Example 14a are introduced into 80 ml of methylene chloride. A mixture of 9.75 g (0.09mol) of 2,6-lutidine and 10.5 g (0.07 mol) of 2-methyl-1-phenyl-2-propanol is added dropwise at 5° C. under argon. The mixture is then stirred for 8 hours at room temperature. The mixture is poured on ice and extracted with hexane. The combined hexane phases are washed with water and then dried with $MgSO_4$. The hexane is removed in vacuo and the residue is subjected to chromatography on silica gel. This gives 16.79 g of a colourless liquid (82% of theory). Boiling point =84°-85° C./0.026 mbar.

Analysis:

(C₁₈H₃₂OSi) calculated: C 73.90; H 11.03; Si 9.60; found: C 73.79; H 11.21; Si 9.80.

EXAMPLE 16

Preparation of

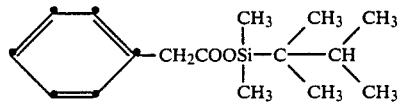

5.0 g (0.037 mol) of phenylacetic acid are added in portions to a solution of 7.8 g (0.044 mol) of (1,1,2,2-tetramethyleth-1yl) dimethylcnlorosilane and 4.8 g (0.047 mol) of triethylamine in 50 ml of dimethylformamide. The mixture is stirred for 2 hours at room temperature and then taken up in hexane and washed with water. The hexane phase is dried with Na₂SO₄ and the evaporation residue is subjected to chromatography on silica gel with hexane/ethyl acetate and then distilled. This gives 6.11 g (59% of theory), boiling point =134°-136° C./2 mbar. The ¹H-NMR spectrum is in agreement with the structure.

EXAMPLE 17

Preparation of

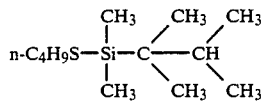

9.1 g (0.09 mol}]f butylmercaptan in 50 ml of hexane are slowly added dropwise to 2.3 g (0.1 mol) of sodium in 50 ml of hexane under argon. The mixture is stirred overnight at room temperature and then heated under reflux for 1 hour. 16.0 g (0.09 mol) of (1,1,2,2-tetramethyleth-1-yl)-dimethylchlorosilane in 25 ml of hexane are then slowly added dropwise, while cooling in an ice bath. After heating under reflux for 2 hours, the mixture is concentrated in vacuo and the residue is distilled This gives 13.2 g of an oil of boiling point 128°-130° C./2.6 mbar. The ¹H-NMR spectrum is in agreement with the structure.

EXAMPLE 18

Preparation of

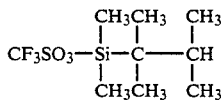

17.85 g (0.1 mol) of (1,1,2,2-tetramethyleth-1-yl)dimethylchlorosilane are introduced under an inert gas into a 50 ml three-necked flask with dropping funnel and reflux condenser. 8.79 ml (0.1 mol ) of trifluoromethanesulfonic acid are added dropwise at room temperature within 10 minutes. The mixture is then heated for 4 hours at 60° C. After the evolution of HCl gas has ceased, the mixture is cooled and then distilled.

23.4 g of the desired silyl ester (80% of theory) are isolated as a colourless liquid, boiling point 39–42° C./0.026 mbar.

EXAMPLE 19

Preparation of

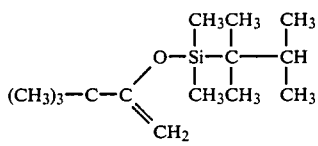

2.0 g (20 mmol) of pinacolin and 2.22 g (22 mmol) of triethylamine are cooled in 20 ml of ether under an inert gas to 0° C. 4.88 g (17 mmol) of (1,1,2,2-tetramethyleth-1-yl)- dimethylsilyl-trifluoromethanesulfonate are added dropwise with stirring at 0°-5° C. Stirring is then continued for a further 4 hours at room temperature The ether phase is separated off and distilled in a bulb tube oven. This gives 3.5 g of a colourless oil (87% of theory), boiling point 105°-110° C./20.8 mbar. ¹H-NMR (CDCl₃, 250 MHz): δ: 0.22 (s. 6H, Si(CH₃)), 0.94 (d, J =6 Hz, 6 H, (CH₃)₂CH); 0.96 (s, 6 H, (CH₂)₂C); 1.06 (s,9 H) C(CH₃)₃); 1.70 (m, 1 H, HC(CH₃)₂), 5.89 (d, J=0.5 Hz, 1 H=CH), 4.03 (d, J=0.5 Hz, 1 H).

EXAMPLE 20

Preparation of

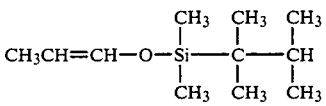

1.16 g (20 mmol) of propionaldehyde and 2.22 g (22 mmol) of triethylamine are cooled in 20 ml of ether under an inert gas to 0° C. 4.88 g (17 mmol) of (1,1,2,2-tetra- methyleth-1-yl)-dimethylsilyl-trifluoromethanesulfonate are added dropwise with stirring at 0°-5° C. Stirring is then continued at room temperature for a further 4 hours. The ether phase is separated off and distilled in a bulb tube oven. This gives 2.45 g of a colourless oil (73% of theory), boiling point 125°-130° C./20.8 mbar.

¹H-NMR (CDCl₃, 250 MH₂): δ: 0.16 (s, 6H, Si(CH₃)₂); 0.90 (s, 6H, (CH₃)₂C); 0.94 (d, J =6 Hz, 6H, (CH₃)₂CH); 1.57 {dd, J =6 Hz, 0,5 Hz, 3H, CH₃CH); 1.65 (m, 1 H, CH(CH₃)₂); 4.60 (m, 1 H =CH-CH₃); 6.17 (m, 1 H, CH-O).

EXAMPLE 21

Preparation of

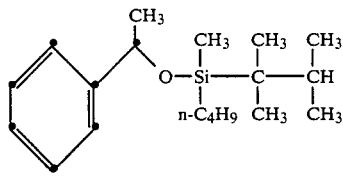

6 4 g (29 mmol) of methyl-butyl-(1,1,2,2-tetramethyleth-1-yl)-chlorosilane are added to a mixture of 2.49 g (36.5 mmol) of imidazole and 2.95 g (24 mmol) of 1-phenylethanol in 30 ml of DMF. After stirring at room temperature for 16 hours, the mixture is worked up as described in Example 8. After distillation in a bulb tube oven, 6.54 g of the desired silyl ether (88% of theory) are isolated as a colourless oil. Boiling point: 115°-120° C./0.26 bar.

EXAMPLE 22

Preparation of

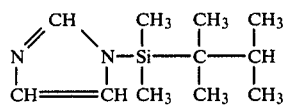

17.9 g (0.1 mol) of (1,1,2,2-tetramethyleth-1-yl)dimethylsilyl chloride, 6.8 g (0.1 mol) of imidazole and 60 ml of triethylamine are added together and stirred for 40 hours at room temperature. The mixture is then diluted with 100 ml of hexane, filtered and concentrated. Distillation of the residue thus obtained gives 17.3 g (82% of theory) of a product of boiling point 79°–81° C./0.065 mbar.

EXAMPLE 23

Preparation of

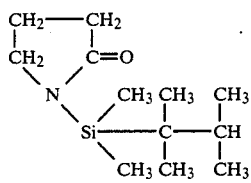

46.1 g (0.26 mol) of (1,1,2,2-tetramethyleth-1-yl)dimethylsilyl chloride, 28.1 g (0.28 mol) of triethylamine and 17 g (0.2 mol) of pyrrolidone are stirred at room temperature for 3.5 hours in 100 ml of dimethylformamide The mixture is then diluted with 200 ml of hexane and washed with ice cold water and 1-molar aqueous oxalic acid. Drying of the hexane phase with sodium sulfate and concentrating gives, after distillation, 40.6 g (90% of theory) of product, boiling point 78°–82° C./0.026 mbar.

EXAMPLE 24

Preparation of

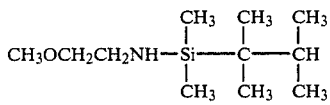

80.7 g (0.8 mol) of triethylamine are added to 20 g (0.27 mol) of 1-amino-2-methoxyethane and 57 g (0.32 mol) of (1,1,2,2-tetramethyleth-1-yl)-dimethylsilyl chloride in 100 ml of hexane and the mixture is stirred at room temperature for 3.5 hours. The mixture is then diluted with 100 ml of hexane and filtered, and the evaporation residue is distilled: 37.7 g (58% of theory) of product of boiling point 54°–58° C./0.065 mbar.

EXAMPLE 25

Preparation of

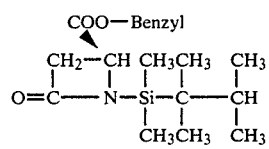

127.0 g of (1,1,2,2-tetramethyleth-1-yl)-dimethylchlorosilane (0.71 mol) are dissolved in 500 ml of dimethylformamide and 72.4 g of triethylamine (0.72 mole) are added. 132.3 g of benzyl (4S)-azetidine-2-one-4-carboxylate (0.645 mol) are then introduced in portions while cooling in a waterbath such that the internal temperature is 25°–30° C. The resulting white, thick suspension is then stirred for 2 hours at room temperature. The mixture is taken up in 1000 ml of hexane and washed successively with 1000 ml of water, 80 ml of 1-molar oxalic acid and 2×1000 ml of water. After drying with sodium sulfate and distilling off the hexane, a slightly yellowish evaporation residue is obtained.

Yield: 225.7 g, corresponding to 99% of theory. A thin-layer chromatogram (silica gel, 2:1 hexane/ethyl acetate as solvent) shows a single product. $R_f$ value: 0.58.

EXAMPLE 26

The silyl ethers listed in the table which follows are cleaved at room temperature under the reaction conditions indicated. The results are shown in the table.

| Reaction conditions | n-Butyl—OSi(CH₃)₂—C(CH₃)₂—CH(CH₃)₂ | cyclohexyl—OSi(CH₃)₂—C(CH₃)₂—CH(CH₃)₂ | CH₃CH₂—C(CH₃)₂—OSi(CH₃)₂—C(CH₃)₂—CH(CH₃)₂ |
|---|---|---|---|
| 1% HCl/ethanol(EtOH) | complete cleavage after 30 minutes | complete cleavage after 137 minutes | no cleavage after 6 hours, 16% cleavage after 72 hours |
| n-Bu₄NF/tetrahydrofuran (THF) | complete cleavage after <3 hours | complete cleavage after about 24 hours | no cleavage |
| THF:acetic acid:H₂O = 1:3:1 | complete cleavage after 24 hours | 20% cleavage after 24 hours 50% cleavage after 48 hours | no cleavage |
| NaOH(5%)/EtOH | no cleavage after 24 hours | stable over 24 hours | no cleavage |
| n-Butyl₄NF on silica gel | complete cleavage after <4 hours | 30% cleavage after 6 hours 85% cleavage after 72 hours | no cleavage |
| 5 equivalents of HF/urea cyclohexane | complete cleavage after about 25 minutes | cleavage complete after 30 minutes | 50% cleavage after 22 hours 67% cleavage after 40 hours |
| BF₃(gas)/cyclohexane | complete cleavage after about 40 minutes | cleavage complete after 40 minutes | cleavage complete after 20 minutes → no alcohol → butene |

EXAMPLE 27

Cleavage of

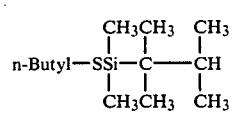

with HCL (b 1%)/ethanol:
  cleavage complete after 24 hours.
With NaOH(5%)/ethanol:
  cleavage complete after 3 hours.

EXAMPLE 28

Cleavage of

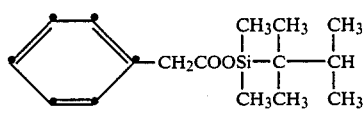

with HCl(1%)/ethanol:
  cleavage complete after <5 minutes
With NaOH(5%)/ethanol:
  cleavage complete after <2 hours

What is claimed is:

1. A compound of formula I

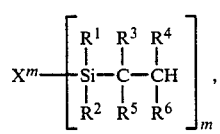

in which X is an ester group of an inorganic or organic acid, m is a number from 1 to 4, $R^1$ and $R^2$ independently of one another are linear or branched $C_1$–$C_{12}$-alkyl, $C_5$-cycloalkyl or $C_6$-cycloalkyl, or $R^1$ and $R^2$ together are tetramethylene or pentamethylene, and $R^3$ and $R^5$ together and $R^4$ and $R^6$ together are tetramethylene or pentamethylene; or $R^3$ and $R^5$ together are tetramethylene or pentamethylene and $R^4$ and $R^6$ are independently linear or branched $C_1$–$C_{12}$-alkyl, $C_5$-cycloalkyl or $C_6$-cycloalkyl; or $R^4$ and $R^6$ together are tetramethylene or pentamethylene and $R^3$ and $R^5$ are independently linear or branched $C_1$–$C_{12}$-alkyl, $C_5$-cycloalkyl or $C_6$-cycloalkyl; or $R^3$ and $R^4$ together and $R^5$ and $R^6$ together are trimethylene or tetramethylene; or $R^3$ and $R^4$ together are trimethylene or tetramethylene and $R^5$ and $R^6$ are independently linear or branched $C_1$–$C_{12}$-alkyl, $C_5$-cycloalkyl or $C_6$-cycloalkyl.

2. A compound according to claim 1, wherein X in formula I is —Cl, —Br or $CH_3SO_3$— or $CF_3SO_3$—.

3. A compound according to claim 1, wherein $R^1$ and $R^2$ in the formula I independently of one another are $C_1$–$C_6$-alkyl.

4. A compound according to claim 3, wherein $R^1$ and $R^2$ are methyl.

5. A compound according to claim 1 wherein $R^3$ and $R^5$ together and $R^4$ and $R^6$ together are pentamethylene; or $R^3$ and $R^5$ together are pentamethylene and $R^4$ and $R^6$ are independently $C_1$–$C_6$-alkyl, cyclopentyl or cyclohexyl; or $R^4$ and $R^6$ together are pentamethylene and $R^3$ and $R^5$ are independently $C_1$–$C_6$-alkyl, cyclopentyl or cyclohexyl; or $R^3$ and $R^4$ together and $R^5$ and $R^6$ together are tetramethylene; or $R^3$ and $R^4$ together are tetramethylene and $R^5$ and $R^6$ are independently $C_1$–$C_6$-alkyl, cyclopentyl or cyclohexyl.

6. A compound according to claim 5 wherein the alkyls $R^3$ to $R^6$ are independently methyl, ethyl, propyl or butyl.

7. A compound according to claim 1, wherein X is Cl or $CF_3SO_3$—, $R^1$ and $R^2$ are methyl and $R^3$ and $R^5$ as well as $R^4$ and $R^6$ are pentamethylene.

8. An improved process for the preparation of a compound of the formula Ia.

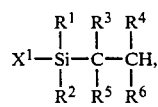

in which X is Cl or Br, $R^1$ and $R^2$ independently of one another are linear or branched $C_1$–$C_{12}$-alkyl, $C_5$-cycloalkyl or $C_6$-cycloalkyl or $R^1$ and $R^2$ together are tetramethylene or pentamethylene and $R^3$ to $R^6$ independently of one another are linear or branched $C_1$–$C_{12}$-alkyl, unsubstituted or $C_1$–$C_6$-alkyl-substituted phenyl or phenyl-$C_nH_{2n}$-with n=1 to 6, $C_5$-cycloalkyl or $C_6$-cycloalkyl, $R^3$ and $R^5$ together and/or $R^4$ and $R^6$ together are tetramethylene or pentamethylene or $R^3$ and $R^4$ together and/or $R^5$ and $R^6$ together are trimethylene or tetramethylene, by addition of a monohalogenosilane of the formula II

in which $R^1$, $R^2$ and $X^1$ are as defined above, to a substituted ethylene in the presence of catalytic amounts of aluminium trichloride, tribromide, oxide chloride or oxide bromide, alkylaluminium dichloride, alkylaluminium dibromide or mixtures thereof at temperatures of at most 60° C., wherein the improvement comprises reacting a tetrasubstituted ethylene of the formula III

in which $R^3$ to $R^6$ are as defined above.

9. A process according to claim 8 wherein the catalyst is alkyl aluminum dichloride or alkyl aluminum dibromide.

* * * * *